United States Patent
Park et al.

[11] Patent Number: 5,877,387
[45] Date of Patent: Mar. 2, 1999

[54] PREPARATION OF PB-SUBSTITUTED HYDROXYAPATITE CATALYST AND USE IN OXIDATIVE COUPLING OF METHANE

[75] Inventors: Tae-Jin Park; Dong Jin Suh; Kwan-Young Lee, all of Seoul, Rep. of Korea

[73] Assignee: Korea Institute of Science and Technology, Seoul, Rep. of Korea

[21] Appl. No.: 862,891

[22] Filed: May 23, 1997

[30] Foreign Application Priority Data

Dec. 12, 1996 [KR] Rep. of Korea ................... 1996-64593

[51] Int. Cl.$^6$ ..................................................... C07C 2/84
[52] U.S. Cl. ........................ 585/943; 585/654; 585/658; 585/502; 585/700; 502/439; 502/208
[58] Field of Search ..................................... 589/943, 654, 589/658, 502, 700; 502/439, 208

[56] References Cited

PUBLICATIONS

Matsumura et al., "Selective oxidative coupling of methane catalyzed over hydroxyapatite ion–exchanged with lead", J. of Chem. Soc., Faraday Trans., 90 (14), 1994.

G.E. Keller and M.M. Bhasin, "Synthesis of Ethylene via Oxidative Coupling of Methane", *Journal of Catalysis,* 73, 9–19 (1982).

B. Hinsen, W. Bytyn and M. Baerns, "Oxidative Dehydrogenation and Coupling of Methane", Proc. 8th ICC, 3, 581–591 (1984).

J.A.S.P. Carreiro and M. Baerns, "Catalytic Conversion of Methane by Oxidative Coupling to $D_{2+}$ Hydrocarbons", *React. Kinet. Catal. Lett.,* vol. 35, Nos. 1–2, 349–360 (1987).

J.P. Bartek, J.M. Hupp, J.F. Brazdil and R.K. Grasselli, "Oxidative Dimerization of Methane over Lead–Magnesium Mixed Oxide Catalysts", *Catalysis Today,* 3, 117–126 (1988).

J.A. Roos, A.G. Bakker, H. Bosch, J.G. van Ommen and J.R.H. Ross, "Selective Oxidation of Methane to Ethane and Ethylene over Various Oxide Catalysts", *Catalysis Today,* 1, 133–145 (1987).

Yasuyuki Matsumura and John B. Moffat, "Catalytic Oxidative Coupling of Methane over Hydroxyapatite Modified with Lead", *Catalysis Letters,* 17, 197–204 (1993).

Kimihiro Yamashita, Hitoshi Owada, Hiroshi Nakagawa, Takao Umegaki and Takahumi Kanazawa, "Trivalent–Cation–Substituted Calcium Oxyhydroxyapatite", *J. Am. Ceram. Soc.,* 69, [8], 590–594 (1986).

*Primary Examiner*—Bekir L. Yildirim
*Attorney, Agent, or Firm*—Darby & Darby

[57] ABSTRACT

A preparation of a Pb-substituted hydroxyapatite catalyst for oxidative coupling of methane represented by the formula $Ca_{10-x}Pb_x$ $(PO_4)_6(OH)_2$ wherein $0<X<10$ or preferably $0<X<3$, includes dissolving calcium nitrate tetrahydrate $[Ca(NO_3)_2 4H_2O]$, lead nitrate $[Pb(NO_3)_2]$ and monobasic ammonium phosphate $[NH_4H_2PO_4]$ in a distilled water at room temperature to have over 0.01M concentration and pH 9 and maintaining a resultant precipitate for 5 to 20 hours for aging and then calcining the resultant. A method for producing $C_2$ compounds using the thusly produced catalyst includes reacting a mixed gas composed of methane, oxygen and helium in the presence of 5~20 g·min/L of the Pb-substituted hydroxyapatite catalyst according to the present invention, at a high temperature of at least 600° C.

10 Claims, No Drawings

PREPARATION OF PB-SUBSTITUTED HYDROXYAPATITE CATALYST AND USE IN OXIDATIVE COUPLING OF METHANE

BACKGROUND OF THE INVENTION

1. Field of the Invention

The present invention relates to a preparation of a Pb-substituted hydroxyapatite catalyst for oxidative coupling of methane in which methane is dimerized at a high yield when a dimerizing reaction is performed for producing ethane and ethylene by partially oxidizing methane which is a major constituent of natural gas with oxygen.

2. Description of the Conventional Art

Methane is the most stable hydrocarbon which is a major constituent of natural gas and much attention has been drawn to methane as a chemical feed stock and an energy source to serve as a substitute for petroleum. Therefore, active studies toward the production of $C_2$ compound by dimerizing methane have been performed. $C_2$ compounds such as ethane and ethylene are very useful as raw material for producing polyethylene and various copolymers of ethylene and propylene or other monomers. Moreover, the dimerization reaction increases the utility of methane to work as a substitute energy source for petroleum, since the $C_2$ compounds are more stable during transportation than methane. When methane is completely combusted, $CO_x$ is formed, and $C_2$ compounds which are intermediate products have higher reactivities with oxygen than methane. Therefore, it is very difficult to selectively obtain $C_2$ compounds under an oxidizing condition.

Many studies have been made for the development of an oxidation catalyst having a high selectivity for the dimerization of methane including *J. Catal.* 73, 9 by G. E. Keller and M. M. Bhasin (1982), and the catalysts representing a comparatively high activity thereof are lithium/magnesium oxide (Li/MgO), samarium oxide ($Sm_2O_3$) and lead oxide/magnesium oxide (PbO/MgO). However, in the case of catalysts well known so far, the yield of $C_2$ compounds is at most about 25%, and in addition, the catalyst is deactivated over the reaction time. Therefore, a commercial process for producing the $C_2$ compounds has not yet been developed.

A supported lead oxide catalyst studied by W. Hinsen, W. Bytyn, M. Baerns (Proc. 8th ICC,3,581 (1984)) is one of the catalysts which have been studied most widely (J.A.S.P. Carreiro and M. Baerns, *Reac. Kinet. Catal. Lett.*, 35,349 (1987)). The activity and selectivity of the catalyst vary depending on the ratio of methane/oxygen, temperature, additives, the support and the Pb-loading. The selectivity for ethylene is high when the lead oxide is supported on a basic oxide or prepared as a complex oxide with a basic oxide. Particularly, the PbO/MgO catalyst exhibits a $C_2$ selectivity as high as 80% on the condition of a lower ratio of oxygen/methane [J. P. Bartek, J. M. Hupp, J. F. Brazdil and R. K. Grasselli, Catal. *Today,* 3,117 (1988)]. However, when the catalytic reaction is carried out at a high temperature in order to achieve a higher conversion, the selectivity is sharply lowered and the lead oxide is evaporated, [J. A. Ross, A. G. Bakker, H. Bosch, J. G. van Ommen and J. R. H. Ross, Catal. *Today,* 1,133 (1987)].

As described previously, for the stabilization of a lead catalyst, studies using a non-volatile salt or a complex oxide have been continued.

Generally, a hydroxyapatite catalyst is a compound which is obtained by the reaction of calcium nitrate tetrahydrate $[Ca(NO_3)_2 4H_2O]$, ammonium phosphate $[(NH_4)_3PO_4]$ and an aqueous ammonia ($NH_4OH$), and a Pb-substituted hydroxyapatite catalyst is the hydroxyapatite catalyst in which lead (Pb) is substituted for calcium (Ca). The Pb-substituted hydroxyapatite catalyst produced by using an ion-exchange method was reported to be active for $C_2$ dimerization reaction. However, the highest yield of the reaction. was no more than 13%, which is not sufficient for commercialization. A Pb-substituted hydroxyapatite catalyst was produced by a cation exchange to be employed in a $C_2$ dimerizing action, but the maximum yield was below 20%, which is also not sufficient [K. Yamashita, H. Owada, H. Nakagawa, T. Umegaki, and T. Kanaawa, *J. Am. Ceram. Soc.*, 69,590(1986)].

SUMMARY OF THE INVENTION

Accordingly, it is an object of the present invention to provide an improved preparation of a Pb-substituted hydroxyapatite catalyst for oxidative coupling of methane represented by the formula $Ca_{10-x}Pb_x(PO_4)_6(OH)_2$, wherein 0<X<10 or preferably 0<X<3 in which the catalyst is stable at a high temperature and its high selectivity is maintained at a high conversion to produce a $C_2$ compound at a high yield.

To achieve the above object, there is provided an improved preparation of a Pb-substituted hydroxyapatite catalyst for oxidative coupling of methane represented by the formula $Ca_{10-x}Pb_x(PO_4)_6(OH)_2$ wherein 0<X<10 or preferably 0<X<3 which includes dissolving a calcium nitrate hydrate $[Ca(NO_3)_2 4(H_2O)]$, lead nitrate $[Pb(NO_3)_2]$ and monobasic ammonium phosphate $[NH_4H_2PO_4]$ in distilled water at room temperature to have a concentration of at least 0.01M and pH 9, maintaining a resultant precipitate for 5 to 20 hours as such in solution to be subjected to aging and then calcining the resultant.

DETAILED DESCRIPTION OF THE INVENTION

According to the present invention, in order to produce a Pb-substituted hydroxyapatite catalyst for methane dimerization by a coprecipitation, experiments were conducted while varying the reaction conditions such as the amount of Pb substitution and the ratio of methane/oxygen, the temperature and the contact time. As a result, compared with the conventional Pb-substituted hydroxyapatite catalyst for methane dimerization produced by an ion exchange method, the catalyst of the present invention was found to produce $C_2$ compound at a high yield of over 20%, by the partial substitution of Pb for Ca.

Description will now be given in detail of the preparation of a Pb-substituted hydroxyapatite catalyst for oxidative coupling of methane represented by the formula $Ca_{10-x}Pb_x(PO_4)_6 (OH)_2$ wherein 0<X<10 or preferably 0<X<3 by slowly adding a predetermined amount of aqueous nitrate solution composed of Ca and Pb into aqueous ammonium phosphate solution. According to the conventional ion-exchange procedure, first a hydroxyapatite is prepared and then is added into a Pb salt aqueous solution to stir for about two hours at room temperature, whereby part of the Ca ions in the hydroxyapatite are replaced by Pb ions. According to the coprecipitation method of the present invention, a predetermined amount of a Ca salt and a Pb salt aqueous solutions are added into an aqueous solution of monobasic ammonium phosphate ($NH_4H_2PO_4$) or dibasic ammonium phosphate $[(NH_4)_2HPO_4]$ slowly to produce the said Pb-substituted hydroxyapatite. The useful Ca salts and Pb salt include a nitrate, an acetate, a carbonate, an aceto acetate, a chloride and a halide. In the coprecipitation reaction according to the present invention, the concentration of the aqueous solution of $[(NH_4)_2HPO_4]$ or $[NH_4H_2PO_4]$, the Ca salt and the Pb salt ranges from 0.01M to a saturated solution and the temperature is used up to 90° C. All the solutions maintain a basicity of at least pH 9 and the rate of adding the Ca salt and Pb salt aqueous solutions depends on the whole amount of solution, but preferably the respective solution of the salt is added as slowly as possible to an extent that an additive amount per minute does not exceed one tenth (1/10) of the whole additive amount. Then, the resulting mixture is refluxed so that an aging is performed on the precipitate for 5 to 20 hours at 90° C. Then the resultant is primarily calcined at a temperature of 200°~500° C. and secondarily calcined at a temperature of 600°~1,000° C. The calcination temperature is slowly elevated at the rate of 1°~20° C./min.

The preparation of a Pb-substituted hydroxyapatite catalyst for oxidative coupling of methane is described in more detail referring to the Examples. However, it is not intended to limit the scope of the present invention to these Examples.

EXAMPLE 1

20.62 g of $Ca(NO_3)_2 4H_2O$ was dissolved in distilled water to prepare 436.55 mL of an aqueous solution (solution A). 1.52 g of $Pb(NO_3)_2$ and 6.34 g of $NH_4H_2PO_4$ were respectively dissolved in distilled water to prepare 23 mL of an aqueous solution (solution B) and 275.7 mL of an aqueous solution (solution C). The concentration of each of the respective aqueous solutions was 0.2M. An appropriate amount of aqueous ammonia was added into the solution C to be adjusted to pH 10.8 and the basic solution put into a flask to stir at a room temperature. Then, the mixture of the solutions A and B was added into the flask at the rate of 2 mL/min, while it was stirred at room temperature. Here, by bubbling the reaction mixture with a pure nitrogen gas, the introduction of carbon dioxide from the air was minimized and the pH was maintained to be in a range of 10.3 to 10.8 using aqueous ammonia. The temperature of the suspension resulting from the mixture of the solutions A and B was elevated up to 90° C. and the suspension was stirred for 16 hours for aging. After three repetitions of filtration and washing, three hours of drying was performed at a temperature of about 110° C. The dried catalyst was primarily calcined at 300° C. for one hour under an atmosphere of oxygen after elevating the temperature up to 300° C. at a rate of 5° C./min. Then, after elevating the temperature up to 800° C. at a rate of 5° C./min, the catalyst was secondarily calcinated at 800° C. for two hours. The catalyst prepared as prescribed has a formula of $Ca_{9.5}Pb_{0.5}(PO_4)_6(OH)_2$.

An experiment for measuring the activity of the catalyst was performed using an "fixed bed atmospheric pressure flow reactor" as follows. 0.36 g of the catalyst prepared as described above having the formula $Ca_{9.5}Pb_{0.5}(PO_4)_6(OH)_2$ was filled in a reaction tube to perform a reaction, providing methane, oxygen and helium at the rates of 8,4 and 25 mL/min, respectively. The temperature was gradually elevated from 725° C. to 800° C. at 25° C. intervals therebetween, and as a result, when the reaction at each temperature reached a steady state, the catalytic activity was measured. At the exit of the reaction tube was provided an ice-water trap for eliminating water resulting from the reaction and the gas mixture passing through the trap was injected into a gas chromatography to be analyzed. As a result of the analysis, ethane, ethylene, carbon monoxide (CO) and carbon dioxide ($CO_2$) as well as methane and oxygen were detected, and after calculating the amount of each product in composition, the sum of the amount of the $C_1$ based products and unreacted methane was set as 100 to determine the methane conversion for each product of the reaction. The total amount of the products was set as 100 to determine the selectivity for each product. Measuring the activity of the Pb-substituted hydroxyapatite catalyst, as shown in Table 1, the result was that the catalyst showed a much higher $C_2$ selectivity with 37~40% of the methane conversion ratio and 18~21% of the yield of $C_2$ compared with a hydroxyapatite catalyst in which Pb was not substituted.

COMPARISON 1

298.8 mL of an aqueous solution containing 23.52 g of $Ca(NO_3)_2 4H_2O$ was slowly added to 498 mL of an aqueous solution containing 6.87 g of $NH_4H_2PO_4$ to prepare a hydroxyapatite catalyst $[Ca_{10}(PO_4)_6(OH)_2]$ in which Pb was not substituted. Using the catalyst, $C_2$ compound was produced, in the way described in Example 1. As shown in Table 1, the result was that the methane conversion was 31~36% and the yield of $C_2$ was 4~14% at a temperature of 725°~800° C.

EXAMPLES 2~7

As in Example 1, by controlling the amount of $Pb(NO_3)_2$ aqueous solution, the Pb-substituted catalyst was prepared such that the value of X in the Pb-substituted catalyst $Ca_{10-x}Pb_x(PO_4)_6(OH)_2$ varied from 0.25 to 4 and each reactive activation was measured. As a result, as shown in Table 1, the yield of $C_2$ with all the catalysts proved higher than when the hydroxyapatite catalyst in comparison 1 was used in which Pb was not substituted.

EXAMPLE 8

Using the Pb-substituted hydroxyapatite catalyst $[Ca_{9.5}Pb_{0.5}(PO_4)_6(OH)_2]$ prepared in Example 1, the catalytic activity was measured at a lower temperature. The reaction conditions other than the reactive temperature was identical to those in Example 1 and the result of the measuring the reactive activation is shown in the Table 2. The result was that the methane conversion was 21~34% and the yield of $C_2$ was 9~19% at a temperature of 650°~700° C.

EXAMPLE 9

Using the Pb-substituted hydroxyapatite catalyst $[Ca_{9.5}Pb_{0.5}(PO_4)_6(OH)_2]$ prepared in Example 1, the catalytic activity was measured at a lower contact time in the same way as in Example 1. Table 2 shows the result of using 0.24 g of the catalyst. The result was that the methane conversion was 36~40% and the yield of $C_2$ was 20~22% at a temperature of 725°~800° C. Although the contact time was lower, an activation effect identical to that in Example 1 was obtained.

EXAMPLE 10

Using the Pb-substituted hydroxyapatite catalyst $[Ca_9Pb(PO_4)_6(OH)_2]$ prepared in Example 1, the reaction experiment was carried out in accordance with an increase in the contact time in the same way as in Example 1. Table 2 shows the result of using 0.60 g of the catalyst. The result was that the methane conversion was 40~44% and the yield of $C_2$ was 21~24% at a temperature of 725°~800° C. Compared with Example 3, although the conversion was increased, the $C_2$ selectivity was maintained at a similar level, resulting in obtaining the $C_2$ compound at a high yield.

COMPARISON 2

The activity and stability at high temperature of the catalyst [$Ca_9Pb(PO_4)_6(OH)_2$] prepared per Example 1 and of the conventional Pb-substituted hydroxyapatite prepared by an ion exchange (Y. Matsumura and J. B. Moffat, *Catal. Today*, 17,197 (1993)) were compared at a temperature of over 700° C.

$Pb_{25}Ap_{1.51}[Ca_{7.6}Pb_{1.46}(PO_4)_6(OH)_2]$ exhibiting the highest catalytic activity was selected as the Pb-substituted hydroxyapatite prepared by an ion exchange according to the method disclosed by Matsumura. Using the two catalysts prepared respectively by the coprecipitation and ion exchange, methane dimerization reaction was carried out for 40 hours at a reaction temperature of 750° C. Table 3 shows the change in the methane conversion and the $C_2$ yield. Over the Pb-substituted hydroxyapatite prepared by coprecipitation according to the present invention, the $C_2$ compound was produced at 38.8% of methane conversion and 21.1% yield, and during the reaction, little change in the activity of the catalyst over time-on-stream was observed. On the contrary, over the Pb-substituted hydroxyapatite prepared by ion exchange, the $C_2$ compound was produced at 25.8% of methane conversion and 16.3% yield at an initial stage of the reaction under the same conditions. As a result of the comparison, it could be seen that the Pb-substituted hydroxyapatite catalyst prepared by ion exchange had a lower activity at an early reaction stage and its activity declined quite rapidly over time-on-stream compared to the catalyst prepared by coprecipitation according to the present invention. That is, it was confirmed that the present inventive catalyst had a higher activity and thermal stability not achievable in the conventional catalyst.

TABLE 1

The Pb substitution effect of hydroxyapatite catalyst on the conversion and selectivity of methane dimerization as well as the yield of $C_2$

| catalyst | RT (°C.) | MC (%) | CO | $CO_2$ | $C_2H_4$ | $C_2H_6$ | $C_2Y$ (%) |
|---|---|---|---|---|---|---|---|
| E1 $Ca_{9.5}Pb_{0.5}$ | 725 | 38.8 | 3.1 | 45.3 | 34.4 | 17.2 | 20.2 |
| $(PO_4)_6(OH)_2$ | 750 | 39.6 | 2.0 | 46.3 | 35.2 | 16.6 | 20.5 |
|  | 775 | 38.7 | 1.3 | 47.6 | 34.3 | 16.8 | 19.8 |
|  | 800 | 37.7 | 1.0 | 49.7 | 33.9 | 15.4 | 18.6 |
| C1 $Ca_{10}(PO_4)_6(OH)_2$ | 725 | 31.3 | 29.2 | 57.2 | 7.6 | 6.0 | 4.3 |
|  | 750 | 32.1 | 26.0 | 52.6 | 13.2 | 8.1 | 6.8 |
|  | 775 | 33.0 | 23.2 | 46.6 | 20.2 | 10.1 | 10.0 |
|  | 800 | 35.9 | 19.8 | 41.3 | 28.7 | 10.3 | 14.0 |
| E2 $Ca_{9.75}Pb_{0.25}$ | 725 | 35.0 | 10.0 | 39.4 | 34.3 | 16.3 | 17.7 |
| $(PO_4)_6(OH)_2$ | 750 | 37.7 | 8.6 | 40.0 | 36.1 | 15.3 | 19.4 |
|  | 775 | 39.0 | 6.5 | 41.8 | 36.7 | 15.0 | 20.2 |
|  | 800 | 39.0 | 2.4 | 45.1 | 37.8 | 14.7 | 20.5 |
| E3 $Ca_9Pb(PO_4)_6$ | 725 | 26.7 | 7.5 | 33.0 | 36.0 | 23.6 | 15.9 |
| $(OH)_2$ | 750 | 35.2 | 8.1 | 36.1 | 38.2 | 17.6 | 19.6 |
|  | 775 | 38.0 | 6.0 | 39.7 | 38.1 | 16.5 | 20.7 |
|  | 800 | 40.8 | 4.5 | 39.7 | 38.9 | 16.9 | 22.8 |
| E4 $Ca_{8.5}Pb_{1.5}$ | 725 | 24.0 | 2.8 | 36.3 | 29.8 | 31.2 | 14.6 |
| $(PO_4)_6(OH)_2$ | 750 | 31.7 | 4.4 | 36.0 | 35.2 | 24.4 | 18.9 |
|  | 775 | 37.8 | 5.0 | 37.7 | 37.7 | 19.6 | 21.7 |
|  | 800 | 38.6 | 4.6 | 42.4 | 37.6 | 15.5 | 20.5 |
| E5 $Ca_8Pb_2(PO_4)_6$ | 725 | 17.8 | 2.8 | 48.1 | 20.4 | 28.7 | 8.7 |
| $(OH)_2$ | 750 | 26.8 | 6.1 | 41.6 | 30.8 | 21.5 | 14.0 |
|  | 775 | 33.0 | 7.2 | 39.8 | 35.6 | 17.4 | 17.5 |
|  | 800 | 38.4 | 5.7 | 41.8 | 37.0 | 15.6 | 20.2 |
| E6 $Ca_7Pb_3(PO_4)_6$ | 725 | 15.2 | 4.7 | 33.6 | 28.6 | 33.1 | 9.4 |
| $(OH)_2$ | 750 | 23.9 | 10.6 | 30.9 | 36.3 | 22.2 | 14.0 |
|  | 775 | 30.3 | 12.0 | 32.3 | 38.6 | 17.1 | 16.9 |
|  | 800 | 34.5 | 11.4 | 35.7 | 38.8 | 14.0 | 18.2 |

TABLE 1-continued

The Pb substitution effect of hydroxyapatite catalyst on the conversion and selectivity of methane dimerization as well as the yield of $C_2$

| catalyst | RT (°C.) | MC (%) | CO | $CO_2$ | $C_2H_4$ | $C_2H_6$ | $C_2Y$ (%) |
|---|---|---|---|---|---|---|---|
| E7 $Ca_6Pb_4(PO_4)_6$ | 725 | 12.3 | 5.5 | 32.9 | 24.9 | 36.7 | 7.6 |
| $(OH)_2$ | 750 | 20.5 | 11.5 | 28.9 | 35.3 | 24.4 | 12.2 |
|  | 775 | 28.5 | 17.1 | 28.0 | 39.1 | 15.9 | 15.7 |
|  | 800 | 34.2 | 17.9 | 30.5 | 39.9 | 11.8 | 17.6 |

*Reaction gas flow rate: $CH_4$ 8 mL/min, $O_2$ 4 mL/min, He 25 mL/min
E: Example
C: comparison
RT: reaction temperature
MC: methane conversion
The amount of catalyst: 0.36 g

TABLE 2

The effect of temperature and contact time of a methane dimerization reaction over the Pb-substituted hydroxyapatite catalyst

| catalyst (amount) | RT °C. | MC (%) | CO | CO | $C_2H_4$ | $C_2H_6$ | $C_2Y$ (%) |
|---|---|---|---|---|---|---|---|
| E8 $Ca_{9.5}Pb_{0.5}$ | 650 | 21.3 | 2.7 | 55.1 | 18.0 | 24.3 | 9.0 |
| $(PO_4)_6(OH)_2$ | 675 | 27.9 | 3.3 | 44.8 | 27.0 | 24.9 | 14.5 |
| (0.36 g) | 700 | 34.0 | 3.8 | 41.8 | 32.2 | 22.2 | 18.5 |
|  | 725 | 38.8 | 3.1 | 45.3 | 34.4 | 17.2 | 20.0 |
| E9 $Ca_{9.5}Pb_{0.5}$ | 725 | 36.2 | 4.4 | 40.6 | 34.5 | 20.6 | 20.0 |
| $(PO_4)_6(OH)_2$ | 750 | 39.4 | 3.8 | 42.1 | 35.4 | 18.8 | 21.3 |
| (0.24 g) | 775 | 39.9 | 3.5 | 42.6 | 36.4 | 17.8 | 21.6 |
|  | 800 | 39.7 | 2.5 | 44.3 | 36.7 | 16.6 | 21.1 |
| E10 $Ca_{9.5}Pb_{0.5}$ | 725 | 40.2 | 3.3 | 42.5 | 36.8 | 17.3 | 21.8 |
| $(PO_4)_6(OH)_2$ | 750 | 43.8 | 1.4 | 44.9 | 36.3 | 17.4 | 23.5 |
| (0.60 g) | 775 | 42.6 | 0.9 | 46.9 | 35.3 | 16.8 | 22.2 |
|  | 800 | 41.2 | 0.8 | 48.1 | 35.2 | 16.0 | 21.1 |

*Reaction gas flow rate: $CH_4$ 8 mL/min, $O_2$ 4 mL/min, He 25 mL/min
E: Example
RT: reaction temperature
MC: methane conversion

TABLE 3

The change of the activity and selectivity in accordance with time-on-stream of the respective pb-substituted hydroxyapatite catalysts prepared by coprecipitation and ion exchange.

| time-on-stream (hr) | | | 0 | 5 | 10 | 20 | 40 |
|---|---|---|---|---|---|---|---|
| CPM | Cop. | M C (%) | 38.8 | 39.7 | 38.0 | 38.2 | 36.8 |
|  |  | $C_2$ Y (%) | 21.2 | 21.9 | 21.2 | 21.4 | 21.1 |
|  | IE | M C (%) | 25.8 | 22.9 | 22.3 | 20.5 | 18.0 |
|  |  | $C_2$ Y (%) | 16.3 | 14.0 | 13.4 | 12.7 | 10.9 |

*Reaction gas flow rate: $CH_4$ 8 mL/min, $O_2$ 4 mL/min, He 25 mL/min
Reaction temperature: 750° C.
CPM: catalyst preparation method
Cop.: coprecipitation
$C_2$ Y: $C_2$ yield
IE: Ion-exchange method
MC: methane conversion Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A preparation of a Pb-substituted hydroxyapatite catalyst for oxidative coupling of methane represented by the formula $Ca_{10-x}Pb_x(PO_4)_6(OH)_2$ wherein $0<X<10$, comprising;

dissolving calcium nitrate tetrahydrate $[Ca(NO_3)_2 \cdot 4H_2O]$, lead nitrate $[Pb(NO_3)_2]$ and monobasic ammonium phosphate $[NH_4H_2PO_4]$ in distilled water at room temperature to have a concentration of at least 0.01M and pH 9; and maintaining a resultant precipitate for 5 to 20 hours as such in the solution and then calcining the resultant.

2. The preparation of claim 1, wherein X ranges $0<X<3$.

3. The preparation of claim 1, wherein the concentration of aqueous calcium nitrate solution ranges from 0.1 to 0.3M.

4. The preparation of claim 1, wherein the concentration of lead nitrate ranges from 0.1 to 0.3M.

5. The preparation of claim 1, wherein the concentration of aqueous monobasic ammonium phosphate solution ranges from 0.1 to 0.3M.

6. The preparation of claim 1, wherein the pH ranges from 10.3 to 10.8.

7. The preparation of claim 1, wherein the calcination is performed in two stages which comprises a first calcination at a temperature of 200°~500° C. and a second calcination at a temperature of 600°~1,000° C. under an oxygen atmosphere.

8. The preparation of claim 7, wherein the calcination temperature is slowly elevated at a rate of 1°~20° C. per minute.

9. A method for producing $C_2$ compounds which is characterized by reacting a mixed gas composed of methane, oxygen and helium in the presence of 5~20 g·min/L of a catalyst prepared according to claim 1 at high temperature of at least 600° C.

10. The method of claim 9, wherein the temperature of the reaction ranges from 700° to 800° C.

* * * * *